United States Patent
Khan et al.

(10) Patent No.: US 6,768,029 B1
(45) Date of Patent: Jul. 27, 2004

(54) OXIDATIVE CLEAVAGE OF UNSATURATED OILS AND PRODUCTS OBTAINED THEREFROM

(75) Inventors: Mohammed Lokman Khan, Gwynedd (GB); Jeremy Tomkinson, Gwynedd (GB); Colin Stanley Fitchett, Cambridge (GB); Mairi Janet Black, Linton (GB)

(73) Assignee: Cambridge Biopolymers Limited, Duxford (GB)

( * ) Notice: Subject to any disclaimer, the term of this patent is extended or adjusted under 35 U.S.C. 154(b) by 0 days.

(21) Appl. No.: 10/018,978

(22) PCT Filed: Jun. 19, 2000

(86) PCT No.: PCT/GB00/02220

§ 371 (c)(1),
(2), (4) Date: Apr. 19, 2002

(87) PCT Pub. No.: WO00/78699

PCT Pub. Date: Dec. 28, 2000

(30) Foreign Application Priority Data

| Jun. 18, 1999 | (GB) | ............................................... 9914101 |
| Jun. 18, 1999 | (GB) | ............................................... 9914103 |
| Jun. 18, 1999 | (GB) | ............................................... 9914106 |
| Jun. 1, 2000 | (GB) | ............................................... 0013329 |

(51) Int. Cl.⁷ ............................................. C07C 45/00
(52) U.S. Cl. ................................................... 568/469
(58) Field of Search ........................................ 568/469

(56) References Cited

U.S. PATENT DOCUMENTS 3,504,038 A * 3/1970 Beal ............................ 568/469

FOREIGN PATENT DOCUMENTS

| EP | 0 235 528 A | 9/1987 |
| WO | WO 00 31015 A | 6/2000 |

OTHER PUBLICATIONS

Pryde et al., JAOCA, vol. 38, pp. 375–379, 1961.*

Pryde E.H. et al.: "Ozonization of Soybean Oil. The Preparation and Some Properties of Aldehyde Oils"; Journal of the American Oil Chemists' Society, US, American Oil Chemists' Society, Champaign, vol. 38, 1961. pp. 375–379, XP 000867112, ISSN: 0003–021X.

* cited by examiner

Primary Examiner—Deborah D. Carr
(74) Attorney, Agent, or Firm—Lahive & Cockfield, LLP

(57) ABSTRACT

The invention provides a solid composite material comprising a matrix formed from a particulate or fibrous material and a cured thermosetting resin, wherein the cured thermosetting resin is derived from an oxidative cleavage product selected from aldehydes and peroxides and mixtures thereof formed by the oxidative cleavage of an unsaturated bond in an unsaturated plant or animal oil, other than the ozonolysis cleavage product of cashew nut shell liquid. Also provided is a process for the production of aldehydes and/or peroxides, which process comprises the treatment of a vegetable oil with ozone (e.g. in the presence of an alcohol as a solvent for the oil) so that hydroperoxides are produced, and the reductive cleavages of the hydroperoxides with a reducing sugar.

31 Claims, No Drawings

OXIDATIVE CLEAVAGE OF UNSATURATED OILS AND PRODUCTS OBTAINED THEREFROM

This invention relates to the preparation of resins from unsaturated oils and to the use of the resins in forming composite and polymeric materials. More particularly, the invention relates to the formation of aldehyde and/or peroxide resin precursors through the oxidative cleavage of unsaturated oils.

BACKGROUND OF THE INVENTION

It is known to use ozonolysis to form aldehyde mixtures from soya oils, see E. H. Pryde et al., The Journal of the American Oil Chemists' Society, page 376, Vol. 38, 1961. Pryde et al disclose that the aldehyde mixtures formed from the ozonolysis are used to form resins with phenol.

The present invention relates primarily but not exclusively to the use of aldehydes derived from the ozonolysis of oils to form various useful industrial products. The invention further provides a number of novel processes for forming aldehydes from oils.

SUMMARY OF THE INVENTION

In a first aspect, the invention provides a solid composite material comprising a matrix formed from a particulate or fibrous material and a cured thermosetting resin, wherein the cured thermosetting resin is derived from an oxidative cleavage product selected from aldehydes and peroxides and mixtures thereof formed by the oxidative cleavage of an unsaturated bond in an unsaturated plant or animal oil, other than the ozonolysis cleavage product of cashew nut shell liquid.

The particulate or fibrous material can be an organic material, for example a lignocellulosic material such as a material selected from wood, straw, hemp, jute, flax, coconut fibre, rice straw and maize. One preferred lignocellulosic material comprises wood particles or wood fibre.

Although particulate or fibrous materials from natural sources are preferred, it is also possible to use fibres or particulate materials of man-made type. For example, such fibres or particles can be formed from polymer compositions, examples being recycled plastics.

The particulate or fibrous material may alternatively (or additionally) be an inorganic material, for example an inorganic material selected from charcoal, marble (e.g crushed marble), mineral fibre, mineral particles, ceramics, crushed rock, clay, coal, slate and glass, e.g. fibre glass.

The solid composite material can take various forms such as, for example, sheet form or moulded form. Examples of composite materials in sheet form are boards and panels, particular examples being wood fibre boards such as chipboard, medium density fibre board (MDF), multilayer boards such as plywood, and building boards and panels.

The measured properties of test wood particle boards in which the binder used has been derived from oxidative cleavage products of the present invention exceed those required for boards to be of a standard acceptable in the marketplace and exceed the European Standards for Internal Bond Strength, Thickness Swell, and Bending Strength (Standards EN 319, EN 317, and EN 310).

In another aspect, the invention provides a solid foam material comprising a matrix formed from a cured resin, wherein the cured resin is derived from an oxidative cleavage product selected from aldehydes and peroxides and mixtures thereof formed by the oxidative cleavage of an unsaturated bond in an unsaturated plant or animal oil.

The foam material typically is formed by reacting the oxidative cleavage product with an isocyanate, for example methylene diphenyl diisocyanate (MDI). Foams formed in accordance with the invention can be used as inter alia insulating materials, upholstery padding and packaging.

In a further aspect, the invention provides resin compositions per se, the resin compositions being derived from an oxidative cleavage product selected from aldehydes, hemi-acetals and peroxides and mixtures thereof formed by the oxidative cleavage of an unsaturated bond in an unsaturated plant or animal oil. In one embodiment, the oil is other than soya oil.

The invention further provides a resin composition as hereinbefore defined and including an acid or base catalyst. Examples of acid catalysts include sulphonic acids, particularly substituted sulphonic acids such as aromatic sulphonic acids, e.g. p-toluene-sulphonic acid. Examples of base catalysts include alkali metal hydroxides, and alkaline earth metal hydroxides, a particular basic catalyst being sodium hydroxide.

Acid and base catalysed cured resins form a further aspect of the invention.

The resins of the invention have a large number of applications, and examples of uses of the resins are in the formation and manufacture of moulded panels, non-woven materials, fibre-glass products, boards, paper treatments, fabric treatments, spun textiles, toys (e.g. children's toys), lubricants, adhesives, castings, automotive components (such as bumpers, fenders, steering wheels, interior panels and mouldings, exterior trim and mouldings), upholstery (as padding or mouldings), binding recycled materials, foundry castings and casting materials (for example binders for refractory articles), bearing, films and coatings, packaging, foams, paint components, pipes, architectural and building products such as door and window frames, varnishes, release controlling coatings such as release controlling coatings for pharmaceuticals, solid prosthetic devices and medical devices, and wood treatment agents, e.g. for preserving and modifying the properties of wood.

Articles of the type listed above, formed from resins derived from an oxidative cleavage product selected from aldehydes and peroxides and mixtures thereof formed by the oxidative cleavage of an unsaturated bond in an unsaturated plant or animal oil represent a further aspect of the invention Plant oils useful in forming the products of the invention include unsaturated plant oils such as tung oil, mono-, di-, and tri-glyceride oils such as oils from oil seed rape, linseed, soya, olive oil, castor oil, mustard seed oil, ground nut oil, and phenolic oils such as cashew nut shell liquid (CNSL).

Oxidation of the oils is preferably effected by ozonolysis, although other oxidative methods suitable for cleaving unsaturated linkages present in the oils to form aldehydes and/or peroxides may also be used. Such alternative methods can include hydrogen peroxide, for example hydrogen peroxide in the presence of a suitable catalyst such as ferrous ions, oxidising metal salts such as periodates and permanganates.

Oxidation of the oils can be carried out in a variety of different solvents which may be either "participating" or "non-participating". Protic solvents such as water or alcohols will tend to participate in the oxidation reaction. For example, the ozonation of unsaturated oils in a protic solvent such as an alcohol or water will lead to formation of a hydroperoxide whereas ozonides are formed in aprotic solvents such as hydrocarbons (e.g. cyclohexane, hexane) and chlorinated hydrocarbons (e.g. dichloromethane and chloroform).

The ozone can be used at concentrations in the range 1 to 10% in oxygen, and typically the treatment with ozone is continued until ozonolysis is complete. The end point for ozonolysis can be judged using thin layer chromatography (TLC), or chemical methods such as the starch iodide test. Such tests are used to check periodically for the end point of the ozonolysis, i.e. when none of the components present in the starting oil are present in the reaction mixture.

Where the oxidation is carried out using ozone, the reaction will typically be carried out at a temperature in the range −78° C. to 60° C., preferably at ambient temperature. Though the temperature of the reaction mixture may rise on introduction of ozone to as high as 45° C. it is preferable to operate at temperatures below 25° C.

After the oxidation (e.g ozonolysis) step, the intermediate ozonides and/or hydroperoxides are subject to cleavage (usually reductive cleavage) to form the aldehyde(s) and optionally hemiacetals thereof (in the case of reactions carried out in alcohols).

Reduction of the ozonolysis reaction products (e.g. ozonides) can be carried out using any of a variety of reducing conditions. Thus, reduction can be effected using a suitable metal, such as a transition metal (e.g. zinc), preferably in the presence of an acid. For example, reduction can be effected using zinc and acetic acid. Alternatively, other methods (e.g. standard methods) of achieving reducing conditions can be used and examples of such methods include catalytic hydrogenation in the presence of a metal catalyst such as a transition metal catalyst; e.g. hydrogen may be bubbled through the reaction mixture in the presence of a catalyst such as Pd-C (catalytic palladium hydroxide on calcium carbonate). Other reducing agents that can be used include iodide (e.g. sodium, potassium, calcium etc)+acetic acid; dimethyl sulphide; thiourea; triphenyl phosphine; trimethyl phosphate and pyridine.

The conditions used to effect reductive cleavage of ozonolysis reaction products have been known for many years but have remained relatively unchanged. Long, in Chemical Reviews 2(1940) page 453, lists various reducing agents for the conversion of peroxidic ozonolysis products to aldehydes and ketones. In a later review, Chemical Reviews 58(1958) page 990, Bailey does not add any additional reducing agents to the list.

The Applicants have now found that a reducing sugar can be used to perform the reductive cleavage of the products formed when oils (e.g. vegetable oils) are treated with ozone in the presence of a solvent which is an alcohol or an alcohol containing solvent.

The use of a sugar for this purpose has a major advantage, in that, unlike most reducing agents, there is no need to separate any residual materials left by their use, and in fact the residues from the use of such sugars can be of benefit when the oxidative cleavage product is used in a curable composition. In the case of zinc powder and acetic acid, zinc powder must be removed.

Catalytic hydrogenation requires a source of hydrogen and the process can involve lengthy reaction times and the use of higher than atmospheric pressures. For example JAOCS 38(1961) includes a procedure at page 379 where hydrogenation in the presence of palladium on charcoal was carried out for 7 hours at atmospheric pressure and for a shorter time (not stated) at 40 p.s.g.i. Reduction with a reducing sugar can be accomplished in shorter times and in a simpler manner.

Thus, according to a further aspect of the invention, there is provided a process for the production of aldehydes and/or peroxides, which process comprises the treatment of a vegetable oil with ozone (e.g. in the presence of an alcohol as a solvent for the oil) so that hydroperoxides are produced, and the reductive cleavage of the hydroperoxides with a reducing sugar.

The reducing sugar can be for example a monosaccharide or a disaccharide, and can be an aldose or a ketose sugar. Particular examples of reducing sugars are hexose monosaccharide sugars such as glucose, mannose, allose, and galactose, and disaccharides such as maltose. A presently preferred sugar is alpha-D-glucose The reductive cleavage is carried out by stirring an aqueous solution of a reducing sugar into the reaction mixture obtained by the ozone treatment. The mixture is then heated to a temperature where reduction takes place at a satisfactory rate to ensure a good yield of aidehyde. The temperature used is conveniently between 50° C. and 60° C. and a time of about two hours is usually sufficient. The product may then be purified to remove substantially all the reacted and any unreacted sugar (if any is present) as described in the Examples below. However, it is preferred simply to remove solvent, and use the aldehyde/peroxide product in admixture with the oxidised sugar and any unreacted sugar remaining. It is further preferred to use excess sugar so that unreacted sugar is present as it is believed, without wishing to be bound by any theory, that the sugar may be of value in stabilising the aldehyde product in storage.

In certain circumstances, for example when the solvent used for the ozonolysis contains water, the use of a reducing agent may not be required.

The present invention can be practised using isolated or purified/semi-purified oils extracted from a suitable plant source. However, in addition, or alternatively, the oil-bearing plant tissues (preferably suitably pre-treated, e.g. comminuted) can be subjected to oxidation to produce a product comprising plant matter containing oxidative cleavage products. For example, plant tissues from that have been extracted to remove the majority of their oil, but still retain a proportion of their oil, can be subjected to oxidative cleavage treatment. The resulting materials can be used to form composites and other products of the type hereinbefore defined. An advantage of this aspect of the invention is that it provides a means of using waste materials that would otherwise be discarded, because of the relatively uneconomic cost of extracting the remaining oil residues.

Accordingly, in another aspect of the invention, there is provided a curable material formed by oxidative treatment of a comminuted oil-bearing plant material, whereby the oxidative treatment has converted unsaturated bonds in the oil into an oxidative cleavage product selected from aldehydes and peroxides and mixtures thereof.

For example, the oil-bearing plant material can be an oil bearing seed, nut or bean, such as oilseed rape, or soya. The oil-bearing plant material is in a comminuted state, for example in the form of a meal prepared by grinding. The meal or other oil-bearing comminuted plant material can contain its full original oil content, or can contain a proportion of its original oil content, the remainder having been extracted.

Thus, for example, in the case of oil seed rape or soya, rape or soya meal that has either its original complement of oil or has been extracted and retains only a proportion of the original oil content, a curable composition is produced that contains the meal as an extender of the composition when used in bonding composites, or forms the matrix of a cast or moulded body.

Curable materials of the type in which the original oil bearing plant tissue is still present in comminuted form can be used to form products of the type described above in relation to resins and composites. The comminuted plant tissue can take the place of, or supplement, the particulate or fibrous materials of the composites. It is envisaged that phenolic residues present in the plant material, for example lignins, may react with the aldehydes and/or peroxides formed by oxidative cleavage of the oils to form phenol-aldehyde bonds, for example.

The oxidative cleavage products (aldehydes, hemiacetals, peroxides and mixtures thereof) formed by the oxidation process can be in the form of oils or solids at ambient temperatures and can subsequently be used either in an undiluted state, or dissolved or dispersed in a suitable solvent or presented as an aqueous emulsion, for example. Addition of an alkali (typically a stoichiometric quantity of alkali such as a metal hydroxide (e.g. NaOH) affords a water soluble compound (possibly a hydrate of the aidehyde) that can be employed in the aqueous state and cured with the addition of an acid catalyst.

Thus, in a further aspect, the invention provides a curable composition comprising an aqueous emulsion or an aqueous alkaline solution containing an oxidative cleavage product selected from aldehydes and peroxides (and optionally hemiacetals) and mixtures thereof formed by the oxidative cleavage of an unsaturated bond in an unsaturated plant or animal oil as hereinbefore defined. The invention further provides a cured composition of the aforesaid type, for example an acid catalysed cured composition.

The compositions of the invention can be cured in a variety of different ways. For example, the compositions are capable of undergoing self-crosslinking through a range of chemistries. The properties of the resulting cured resins or compositions are influenced by the molecular size of the compounds making up the oxidative cleavage product and the number of reactive sites, both being determined by the chain length of the starting material and the degree of unsaturation.

Thus, for example, for aldehyde oxidative cleavage products, crosslinking mechanisms include condensations (e.g.aldol condensations), aidehyde polymerisations, and polymerisation reactions with residual reducing sugars e.g. glucose.

For hydro-peroxide oxidative cleavage products, polymerisation can take place with residual olefin bonds within the oxidative cleavage products, or by means of homo-cross-linking of peroxide or alkyl peroxide moieties.

Curing of the compositions can also be effected by the formation of heteropolymers, for example with compounds such as amines or phenols having free amino or hydroxyl groups, or other nucleophiles.

Heteropolymer coupling partners (e.g.co-monomers) can be incorporated either during the preparation of the oxidative cleavage products or at the curing stage. Suitable species are generally nucleophiles that can cross-link and become incorporated into the resin structure. Such heteropolymers have modified properties resulting from changes to the crosslinking sites and molecular size of the precursors. Useful properties that can be controlled by the choice of additive include: elasticity, rigidity, brittle fracture, toughness, shrinkage, resistance to abrasion, permeability to liquids and gases, UV resistance and absorbance, biodegradability, density and solvent resistance.

The properties of the uncured compositions may also be usefully modified using additives to control, for example, the viscosity and flow characteristics of the compositions on a filler surface or through spray jets. Examples of materials that can be added to the compositions of the invention include aromatics, phenol, resorcinol and other homologues of phenol, cashew nut shell liquid (CNSL), lignins, tannins and plant and other polyphenols, proteins such as soy protein, gluten, casein, gelatin, and blood albumin; glycols and polyols such as ethylene glycol, glycerol and carbohydrates (e.g. sugars and sugar alcohols); amines, amides, urea, thiourea, dicyandiamide, and melamine; isocyanates such as MDI; heterocyclic compounds such as furfural, furfuryl alcohol, pyridine and phosphines.

Homopolymers and heteropolymers formed from the oxidative cleavage products of the plant and animal oils hereinbefore defined constitute a further aspect of the invention.

Polymerisation or curing of the compositions and oxidative cleavage products typically requires a catalyst. Examples of catalysts include acids such as para-toluene sulphonic acid, sulphuric acid, hydrochloric acid and salts that liberate acids, eg ammonium sulphate and ammonium hydrochloride.

Further examples of catalysts include Lewis acids such as zinc chloride and zinc acetate, aluminium compounds such as aluminium chloride and boron compounds such as boron trifluoride (e.g. in its trifluoroboroetherate form), and alkalis such as sodium and potassium hydroxide.

Still further examples of catalysts include radical initiators such as dibenzoyl peroxide or AIBN.

The cured resins typically have curing temperatures in the range 10° C. to 240° C., and undergo curing over periods of 30 seconds or longer (for example up to many hours). Longer curing times aid moulding and spinning for example.

The gel time (i.e. onset of setting during the curing process) can range from 5 seconds to many hours over a temperature range of 20° C. to 140° C. but at ambient temperature (22° C.) is typically of the order of 30 minutes.

The cured compositions of the invention demonstrate excellent water resistance and it has been found that resins used as adhesives in particle boards retain at least half the original internal bond strength after an hour of boiling in water. Resins of the type exemplified below in pure cured resin form have been found to be impermeable to water at 0–100° C.

The heat stability of the cured compositions has also been found to be very high, the degradation temperatures typically falling within the range 180° C.–250° C. Furthermore, the cured compositions and composites made therefrom have good thermal insulation properties and hence are useful in block or foams form as insulating materials. The compositions of the invention have been found to have excellent thermal insulation properties at least as good as conventional polyurethane foams.

A further advantage of the compositions and resins of the invention is that they have low flammability and do not support combustion readily in air. Furthermore, the pyrolysis products of the resins can readily be selected so as not to produce toxic products such as formaldehyde, cyanide, nitrogen oxides or phenol on combustion.

Another advantage of the resins of the invention is that, when used as an adhesive in composite formulations, the resins out perform standard urea formaldehyde (UF) resins and are similar in strength to phenol formaldehyde (PF) and isocyanate resins.

One particular use of the resins of the invention is as adhesives in the manufacture of particle board. In order to test the strength of the resin compositions of the invention, test particle boards can be formed using both the alkali and acid catalysed adhesives. Particle board is formed by pressing a wood particle/adhesive mixture in a die with a pre-heated punch to e.g. 6 mm stops at an elevated temperature for several minutes. It is necessary to ensure that at its core the material being pressed reaches a high enough temperature for a sufficient time to cure the adhesive. The final dimensions of the product depending on the shape of the die and the pressure applied.

The experimental boards are made from wood chips sieved to remove fines below 1 mm and particles greater than 5 mm. The wood has a moisture content of 5.8% (w/w dry wood). Sufficient adhesive is mixed with the wood particles to give a solids content of 14% w/w based on dry wood content. The boards are pressed in a die to give boards with a density of 750 g/m$^3$, a diameter of 312 mm and a thickness of 6 mm. Pressing in the die is carried on for ten minutes at a temperature of 140° C.

DETAILED DESCRIPTION OF THE PREFERRED EMBODIMENTS

The invention will now be illustrated in more detail, but not limited, by reference to the following examples. In the examples, the term "aldehydes" is used to describe the reaction products of the oxidative cleavage process. It is to be understood however that the term "aldehydes" is used in a generic sense and includes within its scope substances other than aldehydes (e.g. hydroperoxides) formed by the process.

EXAMPLE 1

Preparation of Triglyceride Aldehydes
Ozonolysis in dichloromethane using Zinc as Reducing Agent A solution of 400 g (ca. 0.5 mole) of rape seed oil (RSO) in dichloromethane (2 liter) is cooled at −78° C. The solution is stirred with a powerful overhead stirrer. Ozonised oxygen gas containing approximately 33.3 mg of ozone per liter of gas is bubbled through the solution at a rate of 10 liters per minute until one equivalent of ozone has been absorbed (6 hours). The reaction is monitored by TLC (silica gel plate, developed in 20:80 ether and petroleum ether solvent systems). Acetic acid (1 liter) is added followed by the addition of zinc (320 g) while the solution is stirred vigorously. The solution is allowed to warm very slowly to room temperature. Stirring is continued for 2 more hours. Zinc is filtered off at reduced pressure and the oxidised product is extracted from ether/water partition. Ether is removed by evaporation to give the final product (RSO aldehyde, 398.0 g).

EXAMPLE 2

Preparation of Aldehydes from Rape Seed Oil (RSO)
Ozonolysis in Methanol Using Glucose as Reducing Agent A solution of 30 g (ca. 0.08 mole) of RSO in methanol (200 ml) is cooled at −10° C. with overhead stirring. Ozone (at an unknown concentration) in oxygen is bubbled through the solution at the rate of 5 liters/minute until no starting material can be detected by TLC (Silica gel plate, developed in 20:80 ether and petroleum spirit). Alpha-D-Glucose (5 g) is dissolved in alkaline water (pH 10) and added to the ozonation product of RSO with continued vigorous stirring. The solution is allowed to warm slowly to room temperature, and then heated at 60° C. for 2 hours. The product is a off white paste that becomes a solution on addition of acids. The product is extracted repeatedly using a 1. 1 ether/water mixture until a clear solution is observed in the aqueous phase. Removal of the ethereal phase affords RSO aldehydes substantially free of the oxidised sugar formed during the reductive cleavage and any unreacted sugar.

EXAMPLE 3

Ozonolysis of Rape Seed Oil in IMS Using Glucose as Reducing Agent

Rape seed oil (30 g) is dissolved in 200 ml of industrial methylated spirit (IMS) and placed in a reaction vessel with overhead stirring. Ozone in oxygen is bubbled through the solution at a rate of 10 liters per minute until no starting material can be detected by TLC. Alpha-D-Glucose (14 g) is dissolved in 50 ml of water and added to the reaction mixture. The mixture is heated to 50° C. for 2 hours and allowed to cool and left at 25° C. overnight. The solvent is removed under reduced pressure. The RSO aldehydes separate as an oily layer from the water on standing. The oily layer contains oxidised and unreacted sugar.

EXAMPLE 4

Preparation and Testing of Acid Catalysed Adhesive Compositions

Acid catalysed compositions were made up to the formulations shown in Table 1 below and the strengths of the bonds formed by the cured compositions were tested.

The bond strength for acid catalysed composition was measured by specially designed equipment called ABES (Automated Bond Evaluation System). Specially cut and sized veneer of wood is used. Resin was smeared on the test strip on an area of 4 mm×20 mm and pressed with two mini pre-heated platens. After a certain period of time the platens were removed from the bond area, and the bond was cooled by compressed air for 20 seconds, followed by pulling in a shear mode. Pulling continues until the bond failed.

The formulations were tested using a press time of 3 min at 180° C.

TABLE 1

| Formulations | | Bond Strength (mPa) |
|---|---|---|
| Crude RSO aldehyde (Example 2) | 1.0 g | 5 |
| Para-toluene sulphonic acid (p-TSA) | 0.2 g | |
| Extracted RSO aldehyde (Example 1) | 1.0 g | 4.04 |
| p-TSA | 0.2 g | |

The data in Table 1 illustrate that a slightly higher bond strength is obtained in the presence of the oxidised sugar.

EXAMPLE 5

Preparation of Acid Catalysed Composition from RSO Aldehyde

Para-toluene sulphonic acid (0.2 g) is dissolved in 0.2 g of methanol to which 1 g of RSO aldehyde is added. A thin paste is formed by stirring vigorously with a glass rod. By this method, the formulations of Tables 2 and 3 are obtained. The formulations of Table 3 differ from those of Table 2 in that molten maleic anhydride was added.

The formulations listed in Tables 2 and 3 were tested using the ABES apparatus with a press lime of 3 minutes at 180° C. The formulations containing no curing catalyst are included to show that in order to get a satisfactory bond strength, a catalyst is needed.

TABLE 2

Bond strength for acid catalysed RSO resin formulations.

| | Formulations | | Bond strength (mPa) |
|---|---|---|---|
| 1 | RSO aldehyde alone | | 0.4 |
| 2 | RSO aldehyde | 1.0 g | 4.47 |
|   | p-TSA (51% in MeOH) | 0.4 g | |
| 3 | RSO aldehyde | 2.0 g | 4.43 |
|   | p-TSA (51% in water) | 0.4 g | |
| 4 | RSO aldehyde | 4.0 g | 1.35 |
|   | glycerol | 0.2 g | |
| 5 | RSO aldehyde | 4.0 g | 4.16 |
|   | glycerol | 0.2 g | |
|   | p-TSA (51% in water) | 0.4 g | |
| 6 | RSO aldehyde | 5.0 g | 3.86 |
|   | glycerol | 0.4 g | |
|   | p-TSA (51% in water) | 0.4 g | |
| 7 | RSO aldehyde | 6.0 g | 1.84 |
|   | ethylene glycol | 0.2 g | |
| 8 | RSO aldehyde | 7.0 g | 4.08 |
|   | ethylene glycol | 0.2 g | |
|   | p-TSA (51% in water) | 0.4 g | |
| 9 | RSO aldehyde | 8.0 g | 5.01 |
|   | ethylene glycol | 0.4 g | |
|   | p-TSA (51% in water) | 0.4 g | |
| 10 | RSO aldehyde | 1.0 g | 5.56 |
|   | furfuryl alcohol | 0.5 g | |
|   | p-TSA (51% in water) | 0.4 g | |
| 11 | RSO aldehyde | 1.0 g | 5.35 |
|   | furfuryl alcohol | 0.2 g | |
|   | p-TSA (51% in water) | 0.2 g | |
| 12 | RSO aldehyde | 1.0 g | 5.77 |
|   | phenol | 0.5 g | |
|   | p-TSA (51% in MeOH) | 0.4 g | |
| 13 | RSO aldehyde | 1.0 g | 4.81 |
|   | CNSL | 1.0 g | |
|   | p-TSA (51% in MeOH) | 0.4 g | |
| 14 | RSO aldehyde | 1.0 g | 3.36 |
|   | urea | 1.0 g | |
|   | p-TSA (51% in MeOH) | 0.4 g | |

TABLE 3

The Effect of Maleic Anhydride* on Acid Catalysed Resin

| | Formulations | | Bond Strength |
|---|---|---|---|
| 1 | RSO aldehyde alone | | 0.4 |
| 2 | RSO aldehyde | 1.0 g | 4.48 |
|   | p-TSA | 0.2 g | |
| 3 | RSO aldehyde | 0.7 g | 5.31 |
|   | maleic anhydride | 0.3 g | |
|   | p-TSA (solid) | 0.2 g | |
| 4 | RSO aldehyde | 0.7 g | 5.35 |
|   | maleic anhydride | 0.3 g | |
|   | p-TSA (solid) | 0.2 g | |
|   | furfuryl alcohol | 0.2 g | |
| 5 | RSO aldehyde | 0.7 g | 5.51 |
|   | maleic anhydride | 0.3 g | |
|   | glycol | 0.4 g | |
|   | p-TSA (solid) | 0.2 g | |
| 6 | RSO aldehyde | 0.7 g | 5.25 |
|   | maleic anhydride | 0.3 g | |
|   | glycol | 0.4 g | |
|   | p-TSA (solid) | 0.2 g | |
|   | furfuryl alcohol | 0.2 g | |

*The maleic anhydride was added in molten form.

EXAMPLE 6

Preparation of Base Catalysed RSO Aldehyde Compositions

Base catalysed compositions were formulated as shown in Table 4 and were tested using the ABES apparatus with a press time of three minutes and a temperature of 180° C. The bond strengths demonstrated by the compositions are also shown in table 4.

TABLE 4

Base Catalysed RSO Aldehyde Compositions

| | Formulations | | Bond strength (mPa) |
|---|---|---|---|
| 1 | RSO aldehyde alone | 1.0 g | 0.4 |
| 2 | RSO aldehyde | 1.0 g | 1.85 |
|   | NaOH (30%) | 0.4 g | |
| 3 | RSO aldehyde | 1.0 g | 1.8 |
|   | NaOH (13.6%) | 0.4 g | |
| 4 | RSO aldehyde | 1.0 g | 2.38 |
|   | urea | 0.2 g | |
|   | NaOH (30%) | 0.4 g | |
| 5 | RSO aldehyde | 1.0 g | 2.02 |
|   | urea | 0.2 g | |
|   | NaOH (13.6%) | 0.4 g | |
| 6 | RSO aldehyde | 1.0 g | 1.69 |
|   | glycerol | 0.4 g | |
|   | NaOH (13.6%) | 0.4 g | |
| 7 | RSO aldehyde | 1.0 g | 2.43 |
|   | ethylene glycol | 0.4 g | |
|   | NaOH (13.6%) | 0.4 g | |

The compositions were formulated using aqueous NaOH hence the relatively low bond strengths at the pressing times used. Higher bond strengths can be obtained by using pressing times longer times.

EXAMPLE 7

Ozonolysis of Ground Rapemeal

A mixture of 1000 g of ground rape-meal in 2 liters of IMS is maintained at about 20° C. with overhead stirring. Stirring is continued for an hour so as to extract oil into the solvent. Ozone in oxygen is then bubbled through the mixture at 10 liters/min until no soluble starting material can be detected by TLC (silica gel plate, developed in 20:80 ether and petroleum spirit). An aqueous saturated solution of alpha-D-Glucose (33 g) is added to the mixture and held at 40° C. for about 3 hours, whereupon substantially all the solvent is removed under reduced pressure. The meal containing the aldehydes formed by the treatment with the sugar is dried at room temperature and then in an oven at 65° C. to a moisture content of about 4%.

The dried meal (110 g) was mixed with 5 g furfuryl alcohol and 3 g para toluene sulphonic acid and pressed at 180° C. for 3 minutes to form a cured body.

EXAMPLE 8

Formation of Solids and Films from RSO Aldehydes

RSO aldehyde (1 g), prepared as described in Example 3 was mixed with 0.2 g of para toluene sulphonic acid dissolved in water. Furfuryl alcohol (0.2 g) was then added with stirring and the mixture was allowed to stand. The mixture set to a solid plastic material after 4 hours. Another quantity of the mixture was prepared and cast into a film and allowed to set.

EXAMPLE 9

Preparation of Resin Monomers with Fenton's Reagent

Hydrogen peroxide(20 g) is added to 20 g of oil (triglyceride or any other oil with unsaturation in the chain) with stirring and then 0.4 g of protein (e.g. Supro 500E) is added to the mixture with continued stirring. An emulsion is formed. A solution of ferrous sulphate (0.2 g in 10 ml of 0.1N Hydrochloric acid) is added dropwise to the above mixture with stirring. If necessary more hydrogen peroxide and ferrous sulphate is added to the completion of the reaction indicated by TLC. Products are extracted with petroleum ether (bp 40–40° C.) and washed with water several times.

EXAMPLE 10

Ozonolysis of Oil (CNSL or any Alvcerides with Unsaturation in the Chain) in Acetone-water Blend Plant oil (220.5 g) is mixed with 2 liter acetone and 800 ml water. The mixture is cooled to 15° C. and ozone in oxygen is bubled through the mixture with stirring. The progress of the ozonolysis is monitored by TLC (using a solvent mixture of petroleumether (bp 40–60° C.) and diethylether, 4:1, v/v as eluent) and stained with vanillin. The reaction mixture is reduced with 270 g of alpha-D-glucose dissolved in 500 ml of warn water. Acetone is removed under reduced pressure. On standing the mixture separates into two layers, the top layer with products and the bottom layer with water and sugar. When the starting material is cashew nut shell liquid (CNSL), the product is an oil with a range of aldehydes and hydroxy-hydroperoxides. The triglyceride oil affords solid (mp 50° C.) with a range of aldehydes and hydroxyhydroperoxides.

EXAMPLE 10

Ozonolysis of Oil (CNSL or any Glycerides with Unsaturation in the Chain) as Emulsion Plant oil (320 g) is mixed with 3 liters of water and 3.2 g of protein (e.g. Supro 500E) or an equivalent amount of a commercial surfactive agent is added to the mixture. The mixture is stirred vigorously to form an emulsion. The emulsion is cooled to a temperature of around 20° C. and ozone is bubbled through the emulsion until ozonolysis is complete. Ozonolysis is monitored by TLC.

Reduction of the mixture is carried out with 270 g of alpha-D-glucose dissolved in 500 ml of warm water. The product, which is a range of aldehydes and hydroxyhydroperoxide, is extracted with diethylether.

EXAMPLE 11

Ozonolysis of Oil (Glycerides with Unsaturation in the Chain) Blended with Tannin (Plant Polyphenols) or Other Natural Phenolics An amount (441 g) of oil and 441 g of tannin are mixed with 4 liters of acetone and 1 liter water. The mixture is cooled to 15° C. and ozone in oxygen is bubbled through the mixture with stirring. The progress of the ozonolysis is monitored by TLC using a solvent mixture of petroleum ether (bp 40–60° C.) and diethyl ether, 4:1, v/v as the eluent and staining with vanillin. After ozonolysis is complete, the acetone is removed under reduced pressure. The resulting product is a homogeneous mixture of modified oil (a range of aldehydes and hydroxyhydroperoxides) and tannin in water and also some reaction products of modified oil and tannin. Total removal of water affords a solid mixture.

When the acetone-water solvent mixture is replaced by equivalent amount of IMS, the end product of ozonolysis is a mixture of modified oil (a range of aldehydes and hydroxyhydroperoxides) and tannin and also some reaction products of modified oil and tannin. Removal of IMS affords a thick paste.

EXAMPLE 12

Applications of Aldehyde Mixtures Formed by Ozonolysis

EXAMPLE 12A

Resin Roofing Slates

Composite roofing panels are manufactured using a resin as described above in Examples 1 to 11 at a range of addition rates (5%–40%). A blend of inorganic particles described as 'grain' and 'dust' is utilised in varying proportions.

Roofing panels formed in this manner typically exhibited charpy impact strength values of 12 $KJ/M^1$, and flexural modulus values of 8700 MPa

EXAMPLE 12B

Self-leveliing Floor Compound

Samples of a self-levelling compound (CNSL or triglyceride resins in combination with methylene diphenyl diisocyanate (MDI)) were formed.

The resin mixtures containing the MDI were blended with a range of materials e.g. sand, grit to give robust surface properties. The properties of the compositions included a high degree of hydrophobicity and resistance to impregnation by solvents e.g. acetone, dichloromethane. The resins have potential as a binder for substrate for use in laminate flooring.

EXAMPLE 12C

Foam Composition

Samples of low-density expanded foams were manufactured using CNSL and MDI. The mix ratios of the two components ranged from 20:1–1:1.4. The densities of the foams produced ranged from about 50 $kg/m^3$ to 200 $kg/M^3$.

EXAMPLE 12D

Solid Fuel Briquettes

Samples of solid fuel briquettes were manufactured using a cold-cure technique employing CNSL and triglyceride resins with an acid catalyst. The briquettes typically had a crush-strength value after7 days of 19 kN.

EXAMPLE 12E

Wood Preservation

Wood panels were impregnated with dilute solution CNSL aldehyde catalyzed with acid or alkali. CNSL aldehyde is soluble in water when alkali (e.g. sodium hydroxide) is used as catalysts but alcoholic or other organic solvents (e.g. IMS) were required when acid (e.g. para-toluenesulphonic acid) was used as catalyst. The impregnating resins were cured at room temperature and the treated wood panels were found to have superior dimensional stability, water resistance and resistance against wood decaying agents.

EXAMPLE 12F

Wood-based Panels

Wood base panels were manufactured having a resin content of 10%. The properties of the panels were as follows:

CNSL aldehyde (alkali cured)

| Internal Bondstrength | 0.98 Mpa |
|---|---|
| 24 hour thickness swell | 20.4% |

CNSL aldehyde (acid cured)

| Internal Bond strength | 1.05 MPa |
|---|---|
| Internal bond after boiling | 0.54 MPa |
| 24 hour thickness swell | 12.2% |

EXAMPLE 13

Curable Resin Composition Containing Pine Tannin

A curable composition is formed by blending an oxidised triglyceride (produced by ozonolysis), pine tannins and p-TSA in the following proportions:

| oxidised (ozone method) triglycerides | 75.0 g |
|---|---|
| pine tannin | 75.0 g |
| p-TSA | 30.0 g |
| water | 30.0 g |

The blend is formed by dissolving para-toluene sulphonic acid in the water and adding the tannin slowly with stirring. Finally, the oxidised oil is added to the mixture.

EXAMPLE 14

Curable Composition Containing Triglyceride and Phenol

A curable composition is formed by blending an oxidised triglyceride (produced by ozonolysis), phenol and P-TSA in the following proportions:

| oxidised (ozone method) triglycerides | 108.6 g |
|---|---|
| phenol | 41.4 g |
| p-TSA | 30.0 g |
| water | 30.0 g |

The blend is formed by dissolving para-toluene sulphonic acid in the water and adding to melted phenol. Finally, the oxidised oil is added to the mixture.

EXAMPLE 15

Properties of Resin Produced from Oxidised Triglyceride and Pine Tannin

By means of the test method described in Example 4, the bonding strength of the pine tannin-containing composition was determined for varying press times and press temperatures, and the bonding strengths are shown in Tables 5 and 6 below.

TABLE 5

Bonding strengths at various temperatures after a press time of 40 seconds

| Temperature (° C.) | Strength (mPa) |
|---|---|
| 70 | 1.65 |
| 80 | 2.31 |
| 90 | 2.52 |
| 100 | 328 |
| 110 | 5.13 |
| 120 | 5.73 |
| 130 | 4.07 |
| 140 | 4.16 |
| 150 | 4.17 |
| 160 | 4.53 |
| 170 | 4.45 |
| 180 | 4.49 |

TABLE 6

Bonding Strengths for bonds formed at press temperature of 120°

| Time | Strength (mPa) |
|---|---|
| 10 | 2.79 |
| 20 | 2.82 |
| 30 | 4.51 |
| 40 | 5.12 |
| 50 | 4.88 |
| 60 | 4.10 |
| 90 | 4.71 |
| 120 | 4.97 |
| 180 | 4.52 |
| 240 | 4.89 |
| 300 | 4.86 |

It will readily be apparent that numerous modifications and alterations can be made to the processes described in the foregoing examples without departing from the principles underlying the invention, and all such modifications and alterations are intended to be embraced by this application.

What is claimed is:

1. A solid composite material comprising a matrix formed from a particulate or fibrous material and a cured thermosetting resin, wherein the cured thermosetting resin is derived from an oxidative cleavage product selected from aldehydes and peroxides and mixtures thereof formed by the oxidative cleavage of an unsaturated bond in an unsaturated plant or animal oil, other than the ozonolysis cleavage product of cashew nut shell liquid.

2. A solid composite material according to claim 1 wherein the particulate or fibrous material is an organic material.

3. A solid composite material according to claim 2 wherein the organic material is a lignocellulosic material.

4. A solid composite material according to claim 3 wherein the lignocellulosic material is selected from wood, straw, hemp, jute, flax, coconut fibre, rice straw and maize.

5. A solid composite material according to claim 4 wherein the lignocellulosic material comprises wood particles or wood fibre.

6. A solid composite material according to claim 1 wherein the particulate or fibrous material is an inorganic material.

7. A solid composite material according to claim 6 wherein the inorganic material is selected from inorganic particulates and fibres.

8. A solid composite material according to claim 6 wherein the inorganic material is selected from charcoal, marble (e.g. crushed marble), mineral fibre, mineral particles, ceramics, crushed rock, clay, coal, slate and glass, e.g. fibre glass.

9. A solid composite material according to claim 1 in sheet form or molded form.

10. A solid composite material according to claim 9 in the form of a board or panel.

11. A solid composite material according to claim 10 in the form of a wood fibre board.

12. A solid composite material according to claim 10 in the form of a building board or panel.

13. A solid composite material according to claim 1 wherein the oxidative cleavage product is formed y the oxidative cleavage of an unsaturated plant oil.

14. A solid composite material according to claim 13 wherein the plant oil is selected from rapeseed oil, soyabean oil, olive oil, castor oil, mustard seed oil, ground nut oil and linseed oil.

15. A solid composite material according to claim 1 wherein the oxidative cleavage product is formed by ozonolysis of the oil.

16. A solid composite material according to claim 15 wherein the ozonolysis is followed by a reductive cleavage step to form the oxidative cleavage product.

17. A solid composite material according to claim 15 wherein the reductive cleavage step is effected by means of a reducing agent selected from metal/acid reducing agents and reducing sugars.

18. A solid foam material comprising a matrix formed from a cured resin, wherein the cured resin is derived from an oxidative cleavage product selected from aldehydes and peroxides and mixtures thereof formed by the oxidative cleavage of an unsaturated bond in an unsaturated plant or animal oil.

19. A solid foam wherein the oil is as defined in claim 1 or is cashew nut shell liquid.

20. A resin composition, the resin composition being derived from an oxidative cleavage product selected from aldehydes and peroxides and mixtures thereof formed by the oxidative cleavage of an unsaturated bond in an unsaturated plant or animal oil, wherein the oil is other than soya oil.

21. A resin composition according to claim 20 comprising an acid or base catalyst.

22. A resin composition according to claim 21 wherein the resin composition is cured.

23. An article or composition formed from or comprising a resin composition derived from an oxidative cleavage product selected from aldehydes and peroxides and mixtures thereof formed by the oxidative cleavage of an unsaturated bond in an unsaturated plant or animal oil, the article or composition being selected from moulded panels, non-woven materials, fibre-glass products, boards, treated paper, treated fabric, spun textiles, toys (e.g. children's toys), lubricants, adhesives, castings, automotive components (such as bumpers, fenders, steering wheels, interior panels and mouldings, exterior trim and mouldings), upholstery (as padding or mouldings), bonded recycled materials, foundry castings and casting materials (for example binders for refractory articles), bearing, films and coatings, packaging, foams, paint components, pipes, architectural and building products such as door and window frames, varnishes, release controlling coatings such as release controlling coatings for pharmaceuticals, solid prosthetic devices and medical devices, and wood treatment agents, e.g. for preserving and modifying the properties of wood.

24. A curable material formed by oxidative treatment of a comminuted oil-bearing plant maternal, whereby the oxidative treatment has converted unsaturated bonds in the oil into an oxidative cleavage product selected from aldehydes and peroxides and mixtures thereof.

25. A curable material according to claim 24 wherein the oil-bearing plant material is an oil bearing seed, nut or bean, such as oilseed rape, or soya.

26. A curable composition comprising an aqueous emulsion or an aqueous alkaline solution containing an oxidative cleavage product selected from aldehydes and peroxides and mixtures thereof formed by the oxidative cleavage of an unsaturated bond in an unsaturated plant or animal oil, wherein the curable composition is cured.

27. A process for the production of aldehydes and/or peroxide, which process comprises the treatment of a vegetable oil with ozone (e.g. in the presence of an alcohol as a solvent for the oil) so that hydroperoxides are produced, and the reductive cleavage of the hydroperoxides with a reducing sugar.

28. A process according to claim 27 wherein the reducing sugar is a monosaccharide or a disaccharide, for example a hexose monosaccharide sugar such as glucose, mannose, allose, and galactose, or a disaccharide such as maltose.

29. An article or composition according to claim 23 wherein the oil is other than soya oil.

30. An article or composition according to claim 23 wherein the resin composition comprises an acid or base catalyst.

31. An article of composition according claim 23 wherein resin composition is cured.

* * * * *